(12) United States Patent
Farmer et al.

(10) Patent No.: US 12,059,447 B2
(45) Date of Patent: Aug. 13, 2024

(54) OLFACTORY DELIVERY OF THERAPEUTIC COMPOUNDS TO THE CENTRAL NERVOUS SYSTEM

(71) Applicant: Locus Solutions IPCo, LLC, Solon, OH (US)

(72) Inventors: Sean Farmer, North Miami beach, FL (US); Ken Alibek, Solon, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 69 days.

(21) Appl. No.: 16/988,627

(22) Filed: Aug. 8, 2020

(65) Prior Publication Data
US 2021/0038671 A1    Feb. 11, 2021

Related U.S. Application Data

(60) Provisional application No. 62/885,231, filed on Aug. 10, 2019.

(51) Int. Cl.
| | | |
|---|---|---|
| *A61K 9/00* | (2006.01) | |
| *A61K 36/53* | (2006.01) | |
| *A61K 47/10* | (2017.01) | |
| *A61K 47/18* | (2017.01) | |

(52) U.S. Cl.
CPC ............ *A61K 36/53* (2013.01); *A61K 9/0043* (2013.01); *A61K 9/0075* (2013.01); *A61K 9/0078* (2013.01); *A61K 47/10* (2013.01); *A61K 47/183* (2013.01)

(58) Field of Classification Search
None
See application file for complete search history.

(56) References Cited

U.S. PATENT DOCUMENTS

| | | | |
|---|---|---|---|
| 5,443,840 A * | 8/1995 | Morancais | A61K 8/14 428/402.2 |
| 2007/0253941 A1 | 11/2007 | Naidu et al. | |
| 2016/0073944 A1 | 3/2016 | Lazarini et al. | |

FOREIGN PATENT DOCUMENTS

| | | |
|---|---|---|
| CN | 109248194 A | 1/2019 |
| JP | 2006131589 A | 5/2006 |
| KR | 20150037774 A | 4/2015 |
| WO | 9107947 A1 | 6/1991 |
| WO | 2018081411 A2 | 5/2018 |
| WO | 2019023039 A2 | 1/2019 |
| WO | 2019075456 A2 | 4/2019 |
| WO | WO-2019087084 A1 * | 5/2019 ............ A61K 36/53 |

OTHER PUBLICATIONS

Medline Plus, Neurosciences Medical Encyclopedia, Accessed Apr. 15, 2022 (Year: 2022).*
Jimenez "Functional Neurology: What causes Inflammation and Brain Fog?" (accessed online Aug. 9, 2022). (Year: 2022).*
McCoy et al. Journal of Neuroinflammation 2008, 5:45, 1-13). (Year: 2008).*
Morita et al. (Biochimica et Biophysica Acta 1810 (2011) 1302-1308). (Year: 2011).*
Benny, A., et al. "EEssential Oils as Treatment Strategy for Alzheimer's Disease: Current and Future Perspectives." Planta Medica, 2019, 85: 239-248.
Costa, M., et al. "N-acetylcysteine protects memory decline induced by streptozotocin in mice." Chemico-biological interactions 253 (2016): 10-17.

* cited by examiner

*Primary Examiner* — Melissa S Mercier
(74) *Attorney, Agent, or Firm* — SALIWANCHIK, LLOYD & EISENSCHENK

(57) ABSTRACT

The present invention provides materials and methods for treating symptoms of neurological conditions. More specifically, the subject invention provides compositions and methods of their use for treating one or more symptoms and/or comorbidities of a neurological condition such as an infection, a neurodevelopmental disease, and/or a neurodegenerative disease. In preferred embodiments, the composition is administered to the subject via nasal administration.

10 Claims, No Drawings

OLFACTORY DELIVERY OF THERAPEUTIC COMPOUNDS TO THE CENTRAL NERVOUS SYSTEM

CROSS-REFERENCE TO RELATED APPLICATION

This application claims priority to U.S. Provisional Patent Application No. 62/885,231, filed Aug. 10, 2019, which is incorporated herein by reference in its entirety.

BACKGROUND OF THE INVENTION

The causes of many neurological diseases remain disputed; however, it is now accepted that the immune protection of the brain is not absolute and that cells of the central nervous system are sensitive to infections capable of penetrating the blood-brain barrier, to inflammatory events occurring in the periphery, and to the infiltration of peripheral immune cells.

There are many parallels between different neurodegenerative disorders, including atypical protein assemblies, induced cell death, immune function damage, pro-inflammatory responses and oxidative stress. There is also a growing body of evidence that some acute and chronic infections and inflammation processes are common features of neurodegenerative and neurodevelopmental diseases. For example, infections such as viral and bacterial diseases of the respiratory tract, and a number of other viral, bacterial and fungal pathogenic infections could play a role in the development of these pathologies.

Even though there is still controversy as to how the infections play a role in the progression of neurological diseases, there is evidence of how they may lead to damage in both the infected and neighboring cells. The infection leads to the activation of inflammatory processes and host immune responses, which act as defense mechanisms, and which in turn cause damage to the host's neuronal functions and viability. Neurodegenerative damage due to bacterial and viral pathogens has been reported because of, for example, the production and deposit of misfolded protein aggregates, oxidative stress, deficient autophagic processes, and neuronal death. These effects may act in combination with other factors such as aging, metabolic diseases and the genetic makeup of the host to lead to improper neural development and/or neurodegeneration.

The ideal treatment plan for neurological conditions coordinates therapies and interventions that meet the specific needs of the individual; however, the challenge of bypassing the blood-brain barrier (BBB) to allow therapeutic molecules to access the central nervous system (CNS) has been a long-recognized challenge to developing new treatments for neurological disorders.

In general, bioavailability can refer to the rate and extent to which a substance reaches and enters a desired body system of a living organism, and can be effective therein. Specifically, bioavailability in the context of pharmacology is a measure of the rate and extent to which a therapeutic compound reaches a site of action.

The bioavailability of a substance can play an important role in its usefulness for a living organism, and can change based on a variety of factors. For example, many substances can be rejected by P-glycoprotein 1, a protein of the cell membrane that pumps foreign substances out of cells. More formally, it is an ATP-dependent efflux pump with broad substrate specificity. This pump is thought to have evolved as a defense mechanism against harmful substances, but can serve as an obstacle in many cases when a foreign, yet desirable, substance is sought to be introduced into the body. It is broadly distributed and expressed in the cells of a variety of organs, including the intestinal epithelium, where it pumps, for example, xenobiotics, back into the intestinal lumen; in liver cells, where it pumps substances into bile ducts; in the cells of the proximal tubule of the kidney, where it pumps substances into the urine-conducting ducts; and in the brain capillary endothelial cells composing the blood-brain barrier and blood-testis barrier, where it pumps substances back into the capillaries.

Brain capillary endothelial cells join tightly together to form the BBB, which separates the brain from the blood and prevents exposure of the CNS to circulating toxins and chemicals. In normal circumstances, the BBB plays a vital role in protecting the delicate milieu of the brain; however, when the introduction of exogenous treatment into the CNS is desired, the BBB prevents 98% of small-molecules and an even greater percentage of large molecules from reaching their intended targets. This lack of access to the brain is a major bottleneck for CNS drug development. Researchers with promising concepts have been forced to discard innumerable drugs with high therapeutic potential due to their inability to deliver the medication across the BBB in therapeutic concentrations and, thus, their inability to reach the target sites.

One recently-conceived approach to treating neurologic disorders is through olfactory delivery. The adult human nasal cavity is covered by respiratory epithelium, across which systemic drug absorption can be achieved. The olfactory epithelium is located in the upper posterior region of the nasal cavity. The nerve cells of the olfactory epithelium project into the olfactory bulb of the brain, which provides a direct connection between the brain and the external environment. If therapeutic compounds can be transferred along the olfactory nerve cells and/or along the perineural space surrounding the olfactory nerve cells into the CSF, they can bypass the BBB and enter the brain and other parts of the CNS directly.

Evolutionary obstacles hinder the bioavailability of certain compounds and nutrients from reaching the CNS for treatment of neurological conditions. Thus, there is a continuing need for new, integrated compositions and methods for treating a broad range of neurological symptoms and improving the overall quality of life and performance for patients diagnosed with neurological conditions.

BRIEF SUMMARY OF THE INVENTION

The present invention provides materials and methods for treating neurological conditions, their symptoms, and/or their causes. More specifically, the subject invention provides compositions and methods of their use for treating, for example, a neurological condition, infections, neurodevelopmental diseases, and/or a neurodegenerative diseases. Advantageously, compositions and methods of the subject invention are non-toxic and cost-effective.

In certain specific embodiments, the subject invention provides approaches to enhancing bioavailability of a health-promoting substance using microbial growth by-products by, for example, suppressing P-glycoproteins and/or modulating other barrier mechanisms that would otherwise reduce the penetration of certain substances into, for example, a subject's epithelial cells and/or across the blood-brain barrier (BBB).

In preferred embodiments, compositions are provided for treating one or more symptoms of a neurological condition.

Advantageously, the present compositions comprise components that improve the bioavailability of the composition to the central nervous system (CNS) by, for example, penetrating the nasal epithelial cells and by crossing the BBB.

In a preferred embodiment, the composition comprises one or more biological amphiphilic molecules (BAM), wherein the BAM are preferably biosurfactants selected from, for example, low molecular weight glycolipids (e.g., sophorolipids, rhamnolipids, mannosylerythritol lipids, cellobiose lipids, and trehalose lipids), lipopeptides (e.g., surfactin, iturin, fengycin, arthrofactin and lichenysin), flavolipids, phospholipids (e.g., cardiolipins), fatty acid ester compounds, fatty acid ether compounds, and high molecular weight polymers such as lipoproteins, lipopolysaccharide-protein complexes, and polysaccharide-protein-fatty acid complexes.

Biosurfactants are surface-active substances produced by microorganisms that lower the surface tension (or interfacial tension) between two liquids or between a liquid and a solid. All biosurfactants are amphiphiles. They consist of two parts: a polar (hydrophilic) moiety and non-polar (hydrophobic) group. Due to their amphiphilic structure, biosurfactants increase the surface area of hydrophobic water-insoluble substances, increase the water bioavailability of such substances, and change the properties of bacterial cell surfaces. Furthermore, biosurfactants accumulate at interfaces, and reduce the surface and interfacial tension between the molecules of liquids, solids, and gases, thus leading to the formation of aggregated micellar structures in solution.

Biosurfactants help serve as a carrier, an adjuvant and/or an active ingredient in the present compositions. They can help suppress and/or modulate the activity of, for example, blood plasma proteins, P-glycoproteins, and other barriers (e.g., the BBB) and cell junctions that prevent certain compounds from penetrating into the brain and other parts of the nervous system. Additionally, in some embodiments, the biosurfactants can have antiviral, antibacterial, anti-biofilm, anti-inflammatory, and immunomodulatory properties.

In certain embodiments, the biosurfactants are glycolipids, such as sophorolipids. The one or more biosurfactants can further include any one or a combination of: a modified form, derivative, fraction, isoform, isomer or subtype of a biosurfactant, including forms that are biologically or synthetically modified. In certain embodiments, the one or more biosurfactants are isolated and/or purified.

In one embodiment, the one or more biosurfactants are present in the composition in critical micelle concentration (CMC), or if treatment of a bacterial infection is desired, at least the minimum inhibitory concentration (MIC). In certain embodiments, the amount of biosurfactant(s) in the composition is about 250 μg/ml to about 800 μg/ml, or about 500 μg/ml to about 700 μg/ml.

The composition can further comprise one or more essential oils and/or plant extracts. Preferably, the essential oils and/or plant extracts comprise compounds having antiviral, antibacterial, anti-biofilm, anti-inflammatory, and/or immunomodulatory properties, such as, for example, terpenes and/or phenols. In a specific embodiment, the composition comprises about 0.1 to about 5 ml/L each of *eucalyptus* oil, clove oil, and/or tea tree oil.

In some embodiments, the composition can further comprise one or more additional neuroprotective agents, such as antioxidants. Antioxidants include, for example, N-acetyl-L-cysteine, flavonoids, (e.g., anthocyanin, caffeic acid, catechin and quercetin), Vitamin E, tocotrienol, glucosinolates, isothiocyanates, and/or polyphenols. In certain embodiments, the composition comprises about 0.05 to about 1 gram/L of N-acetyl-L-cysteine.

The composition may have other components including, for example, carriers, pH modifiers, buffers, local anesthetic agents, agents that promote wound healing, agents that help degrade biofilm, agents that stop bleeding and/or promote clot formation, smoothing agents, emulsifiers, carriers, and other therapeutic and non-therapeutic components.

In one embodiment, the subject invention provides a delivery system, wherein the BAM of the composition form a liposome or nanocapsule with the other components of a nasally-administered composition encapsulated therein. In one embodiment, additional biological polymers can be included to provide further structure for the nanocapsule.

This delivery system can enhance the bioavailability of therapeutic compounds by protecting the compounds from components in the blood, such as proteins and other molecules, that otherwise might bind to and/or degrade the compounds and prevent them from arriving at a target site, e.g., the brain. Additionally, the nanocapsule delivery system allows for time release of therapeutic compounds, thereby providing longer lasting therapeutic effects while reducing potential toxicity or potential negative side-effects of compounds in a subject.

The present invention further provides a method of treating a neurological condition, wherein the method comprises administering a therapeutically-effective amount of a composition according to the present invention to a subject in need thereof. In preferred embodiments, the composition is administered to the subject nasally. The olfactory bulb is closely connected to the cerebrospinal fluid (CSF), thus providing a route for nasally-administered therapeutic compounds to the brain and other parts of the nervous system.

In preferred embodiments, the composition is administered into the subject's nasal cavity about 4 to 5 times per day, until symptoms improve.

In some embodiments, the method comprises diagnosing the subject with a neurological condition and/or a symptom thereof prior to treating the subject according to the present invention. Neurological conditions include, for example, infections affecting the brain and/or nervous system, neurodevelopmental diseases, and neurodegenerative diseases.

Advantageously, the materials and methods of the present invention can help improve the quality of life for individuals who are either suffering from a neurological condition, or who are currently unaffected by a symptom but wish to prevent the occurrence and/or onset thereof.

DETAILED DESCRIPTION OF THE INVENTION

The present invention provides materials and methods for treating neurological conditions. More specifically, the subject invention provides compositions and methods of their use for treating neurological conditions, infections, neurodegenerative diseases, and/or neurodevelopmental diseases. Advantageously, compositions and methods of the subject invention are non-toxic and cost-effective.

In preferred embodiments, compositions are provided for treating one or more symptoms of a neurological condition. Advantageously, the present compositions comprise components that improve the bioavailability of the composition to the central nervous system (CNS) by, for example, penetrating the nasal epithelial cells and by crossing the blood-brain barrier (BBB). Methods of treating a symptom of a neurological condition are also provided, wherein a therapeutically-effective amount of the composition is administered, via the nasal cavity, to a subject in need thereof.

Selected Definitions

The term "subject," as used herein, describes mammals, including humans, who exhibit one or more symptoms or one or more neurological conditions (e.g., neurodevelopmental disease, neurodegenerative disease, and/or neurological infection). Mammalian species that can benefit from the disclosed methods of treatment include, but are not limited to, apes, chimpanzees, orangutans, humans, monkeys, and other animals such as dogs, cats, horses, cattle, pigs, sheep, goats, mice, rats, guinea pigs, and hamsters. Preferably, the subject is a human of any age and/or any gender.

In one embodiment, the subject is a human exhibiting symptoms of a neurodevelopmental disease, such as, for example, autism spectrum disorder (ASD), intellectual and developmental disability (IDD), developmental coordination disorder, stereotypic movement disorder, Tourette's syndrome, cerebral palsy (CP), fragile-X syndrome, Down syndrome, ADHD, schizophrenia, schizotypal disorder, and/or fetal alcohol spectrum disorder;

a neurodegenerative disease such as dementia, Alzheimer's disease (AD), Parkinson's disease (PD), Lewy body disease, corticobasal degeneration, corticobasal ganglionic degeneration, multiple system atrophy (MSA), progressive supranuclear palsy (PSP), postencephalitic parkinsonism, Hallervorden-Spatz syndrome, Parkinsonism-dementia complex (PDC) of Guam, Huntington's disease (HD), amyotrophic lateral sclerosis (ALS), multiple sclerosis (MS), prion diseases, prion protein amyloid antipathy, Creutzfeldt-Jakob disease, Gerstmann-Straussler-Scheinker syndrome, frontotemporal dementia, Pick's disease, primary progressive aphasia, and semantic dementia, Niemann-Pick disease type C, dementia pugilistica (or chronic traumatic encephalophathy (CTE)), Batten disease (or neuronal ceroid lipofuscinosis (NCL)), Friedreich's ataxia, Spinocerebellar ataxia (SCA), Spinal muscular atrophy (SMA), Argyrophilic grain disease, non-Guamanian motor neuron disease with NFT, subacute sclerosing panencephalitis (SSPE), and/or myotonic dystrophy; and/or an infection affecting the nervous system, such as tuberculosis, leprosy, neurosyphilis, bacterial meningitis, Lyme disease, brain abscesses, neuroborreliosis, viral meningitis, encephalitis, rabies, varicella-zoster virus, measles, poliomuelitis, poliovirus, acquired immunodeficiency syndrome (AIDS), Creutzfeldt-Jakob disease, kuru, Herpesviridae viruses, and influenza A.

The identification of subjects who are in need of treatment for, or prevention of, a neurological condition is well within the knowledge and ability of one skilled in the art. By way of example, a clinician skilled in the art can readily identify, by the use of clinical tests, genetic tests, neurologic and physical examination, and/or medical/family history, those patients who are suffering from a neurological condition as well as those who are predisposed to developing a neurological condition and thus readily determine if an individual is in need of treatment and/or prevention. For instance, neurofibrillary tangles or senile plaques present in neuronal cells and/or cell processes can be determined using electron microscopy (EM) or other clinical techniques known in the art. In addition, spinal fluid or cerebral fluid samples or tissues samples from hippocampal tissue or frontal cortex tissue samples may be obtained from a subject and levels of protein tau present in the samples can be determined using routine techniques such as enzyme-linked immunosorbant assay (ELISA), western blot, and immunological assays.

As used herein, "infection" refers to the introduction and/or presence of a disease-causing, or pathogenic, organism into and/or in another organism, tissue or cell.

As used herein, a "biofilm" is a complex aggregate of microorganisms, such as bacteria or fungi, wherein the cells adhere to each other and/or to a surface. The cells in biofilms are physiologically distinct from planktonic cells of the same organism, which are single cells that can float or swim in liquid medium.

As used herein "preventing" or "prevention" of a situation or occurrence means delaying, inhibiting, suppressing, forestalling, and/or minimizing the onset or progression thereof. Prevention can include, but does not require, indefinite, absolute or complete prevention, meaning the situation or occurrence may still develop at a later time. Prevention can include reducing the severity or intensity of the onset of such a situation or occurrence, and/or inhibiting the progression thereof to a more severe or intense situation or occurrence.

As used herein, "treating" or "treatment" of a symptom of a disease, condition or disorder means the eradicating, improving, reducing, ameliorating or reversing of the symptom. Treatment can include, but does not require, a complete cure of the symptom, meaning treatment can also include partial eradication, improvement, reduction, amelioration or reversal.

As used herein, "control" in the context of a microorganism refers to killing and/or eradicating a microorganism, or otherwise reducing the population numbers and/or inhibiting pathogenicity or further growth of the microorganism at a particular site. In one embodiment, when a microorganism and/or a biofilm has caused an infection, controlling the microorganism and/or biofilm can be a form of treatment.

The terms "effective amount," and "effective dose" are used in this disclosure to refer to an amount of a compound or composition that, when administered to a site, is capable of providing a desired effect at the site. The actual amount of the compound or composition will vary depending on a number of factors including, but not limited to, the severity of the symptoms, the size and health of the subject, and the route of administering the compound or composition.

A plant "extract," as used herein, refers to the material resulting from exposing a plant part to a solvent and removing the solvent, or from using various chemical, immunological, biochemical or physical procedures known to those of skill in the art, including but not limited to, precipitation, steam distillation, centrifugation, filtering, column chromatography, detergent lysis and cold pressing (or expression). Plant extracts can include, for example, essential oils. Plant material can include roots, stems, leaves, flowers, or parts thereof.

The terms "isolated" or "purified," when used in connection with biological or natural materials such as nucleic acid molecules, polynucleotides, polypeptides, proteins, organic compounds, such as small molecules, microorganism cells/strains, or host cells, means the material is substantially free of other compounds, such as cellular material, with which it is associated in nature. That is, the materials do not occur naturally without these other compounds and/or have different or distinctive characteristics compared with those found in the native material.

In certain embodiments, purified compounds are at least 60% by weight the compound of interest. Preferably, the preparation is at least 75%, more preferably at least 90%, and most preferably at least 99% or 100% (w/w) of the desired compound by weight. Purity is measured by any appropriate standard method, for example, by column chromatography, thin layer chromatography, or high-performance liquid chromatography (HPLC) analysis.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Use of the term "comprising" contemplates other embodiments that "consist" or "consist essentially" of the recited component(s).

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof. All references cited herein are hereby incorporated by reference in their entirety.

Nasally-Administered Composition

In preferred embodiments, compositions are provided for treating one or more neurological conditions, and/or causes or symptoms thereof. Advantageously, the present compositions comprise components that improve the bioavailability of the composition to the central nervous system (CNS) by, for example, penetrating the nasal epithelial cells and by crossing the blood-brain barrier (BBB).

In a preferred embodiment, the composition comprises one or more biological amphiphilic molecules (BAM), wherein the BAM are biosurfactants selected from, for example, low molecular weight glycolipids (e.g., sophorolipids, rhamnolipids, mannosylerythritol lipids, cellobiose lipids, and trehalose lipids), lipopeptides (e.g., surfactin, iturin, fengycin, arthrofactin and lichenysin), flavolipids, phospholipids (e.g., cardiolipins), fatty acid ester compounds, fatty acid ether compounds, and high molecular weight polymers such as lipoproteins, lipopolysaccharide-protein complexes, and polysaccharide-protein-fatty acid complexes.

The one or more biosurfactants can further include any one or a combination of: a modified form, derivative, fraction, isoform, isomer or subtype of a biosurfactant, including forms that are biologically or synthetically modified.

Biosurfactants are surface active compounds that lower the surface and interfacial tension between individual molecules at respective surfaces and interfaces. Among other capabilities, biosurfactants provide additional immune support against viral infections, and enhance the bioavailability of the other active components.

Biosurfactants are biodegradable and can be produced using selected organisms on renewable substrates. Microbial biosurfactants are produced by a variety of microorganisms, such as, for example, *Pseudomonas* spp. (*P. aeruginosa, P. putida, P. florescens, P. fragi, P. syringae*); *Flavobacterium* spp.; *Bacillus* spp. (*B. subtilis, B. pumillus, B. licheniformis, B. amyloliquefaciens, B. cereus*); *Wickerhamomyces* spp. (e.g., *W. anomalus*), *Candida* spp. (e.g., *C. albicans, C. rugosa, C. tropicalis, C. lipolytica, C. torulopsis*); *Rhodococcus* spp.; *Arthrobacter* spp.; *Campylobacter* spp.; *Corynbacterium* spp.; *Pichia* spp. (e.g., *P. anomala, P. guilliermondii, P. occidentalis*); *Starmerella* spp. (e.g., *S. bombicola*); and so on.

All biosurfactants are amphiphiles. They consist of two parts: a polar (hydrophilic) moiety and non-polar (hydrophobic) group. The hydrocarbon chain of a fatty acid acts as the common lipophilic moiety of a biosurfactant molecule, whereas the hydrophilic part is formed by ester or alcohol groups of neutral lipids, by the carboxylate group of fatty acids or amino acids (or peptides), organic acid in the case of flavolipids, or, in the case of glycolipids, by the carbohydrate.

Due to their amphiphilic structure, biosurfactants increase the surface area of hydrophobic water-insoluble substances, increase the water bioavailability of such substances, and change the properties of bacterial cell surfaces. Biosurfactants accumulate at interfaces, thus reducing interfacial tension and leading to the formation of aggregated micellar structures in solution. The amphiphilic structure of biosurfactants allows for self-association and to interaction with biological membranes. The ability of biosurfactants to form pores and destabilize biological membranes permits their use as antibacterial, antifungal, and hemolytic agents. Combined with the characteristics of low toxicity and biodegradability, biosurfactants are advantageous for use in a variety of application, including human health.

In one embodiment, the biosurfactants according to the present invention are glycolipids, such as, for example, rhamnolipids, rhamnose-d-phospholipids, trehalose lipids, trehalose dimycolates, trehalose monomycolates, mannosylerythritol lipids, cellobiose lipids, ustilagic acid and/or sophorolipids (including lactonic and/or acidic forms).

In one embodiment, the biosurfactants can comprise one or more lipopeptides, such as, for example, surfactin, iturin, fengycin, arthrofactin, viscosin, amphisin, syringomycin, and/or lichenysin.

In one embodiment, the biosurfactants can comprise one or more other types of biosurfactants, such as, for example, cardiolipin, emulsan, lipomanan, alasan, and/or liposan.

In preferred embodiments, the composition comprises a glycolipid biosurfactant. In a specific embodiment, the glycolipid is a purified SLP. SLP have antibacterial activity against, for example, *Escherichia coli, Moraxella* sp., *Ralstonia eutropha, Rhodococcus erythropolis*, and *Salmonella choleraesuis*. Additionally, SLP can inhibit microbial quorum sensing and destroy biofilms and/or inhibit their formation. This is particularly useful for treating infections, as biofilm formation by viruses and bacteria allows them to develop resistance to drugs and enhances their pathogenicity.

In some embodiments, the composition comprises a lipopeptide biosurfactant. In a specific embodiment, the lipopeptide biosurfactant is surfactin. Lipopeptides are produced by a variety of probiotics and non-pathogenic bacteria, such as, e.g., *Bacillus natto, Bacillus coagulans, Bacillus subtilis, Bacillus amyloliquefaciens*, lactic acid bacteria, and others.

Surfactin, in particular, is one of the most powerful lipopeptide biosurfactants. Surfactin is indicated as having antimicrobial, antitumor, antiviral and antiadhesive properties. It can inhibit fibrin clot formation, induce formation of ion channels in lipid bilayer membranes, and inhibit cyclic adenosine monophosphate (cAMP).

In one embodiment, the BAM can comprise one or more microbial-produced fatty acid ester compounds and/or fatty acid ether compounds having physical properties and/or behaviors similar to those of biosurfactants, but which are not commonly known as biosurfactants.

In certain embodiments, the fatty acid ester compounds can include, for example, highly esterified oleic fatty acids, such as oleic fatty acid ethyl esters and/or oleic fatty acid methyl esters (FAME).

In one embodiment, the BAM is a saponin. Saponins are surfactants that are found in many plants and that exhibit similar characteristics to microbial biosurfactants, for example, self-association and interaction with biological membranes. There are three basic categories of saponins, including triterpenoid saponins, steroidal saponins, and steroidal glycoalkaloids.

Some well-known triterpenoid saponin-accumulating plant families include the *Leguminosae, Amaranthaceae, Apiaceae, Caryophyllaceae, Aquifoliaceae, Araliaceae, Cucurbitaceae, Berberidaceae, Chenopodiaceae, Myrsinaceae* and *Zygophyllaceae*, among many others. Legumes such as soybeans, beans and peas are a rich source of triterpenoid saponins. The steroidal saponins are typically found in members of the *Agavaceae, Alliaceae, Asparagaceae, Dioscoreaceae, Liliaceae, Amaryllidaceae, Bromeliaceae, Palmae* and *Scrophulariaceae* families and accumulate in abundance in crop plants such as yam, alliums, asparagus, fenugreek, yucca and ginseng. The steroidal glycoalkaloids are commonly found in members of the *Solanaceae* family including tomato, potato, aubergines and capsicum.

Many saponins and other biosurfactants can inhibit P-glycoproteins (P-gps). P-gp is a member of the ATP-dependent membrane transport proteins and is known to pump substrates out of cells in ATP-dependent mechanisms. The over-expression of P-gp in tumor cells reduces intracellular drug concentrations, which decreases the efficacy of a broad spectrum of antitumor drugs. Accordingly, inhibiting P-gp potentially enhances the cellular bioavailability of some of these compounds.

Thus, in some embodiments, biosurfactants, such as saponins, contribute to the effectiveness of the composition by, for example, enhancing the bioavailability of the other compounds present in the composition.

Biosurfactants help serve as a carrier, an adjuvant and/or an active ingredient in the present compositions. They can help suppress and/or modulate the activity of, for example, blood plasma proteins, P-glycoproteins, and other barriers (e.g., the BBB) and cell junctions that prevent certain compounds from penetrating into the brain and other parts of the CNS. Additionally, in some embodiments, the biosurfactants can have antiviral, antibacterial, anti-biofilm, anti-inflammatory, and immunomodulatory properties.

In one embodiment, the one or more biosurfactants are present in the composition in critical micelle concentration (CMC), or if treatment of a bacterial infection is desired, at least the minimum inhibitory concentration (MIC). In certain embodiments, the amount of biosurfactant(s) in the composition is about 250 µg/ml to about 800 µg/ml, or about 500 µg/ml to about 700 µg/ml.

In one embodiment, the biosurfactants of the present composition are anti-inflammatory due to suppression of increased expression of IFN-γ, IL-6, iNOS, nitric oxide and downregulation of the LPS-induced TLR4 protein expression of macrophages.

In one embodiment, the biosurfactants of the present composition can modulate the immune system function and response by increasing production of cytokines and other mediators to establish a more anti-inflammatory state; suppressing T cells proliferation with down-regulation of amounts of activated CD8(+) T cells (which produce TNF-α and IFN-γ); increasing CD4(+) CD25(+) regulator T cells (Tregs); and increasing IL-10 switching of the immune response from Th1- to Th2-type.

In one embodiment, the biosurfactants of the present composition can form pores in membranes to improve penetration into cells, tissues and organs. For example, in one embodiment, the biosurfactants can help detach the tight junctions of the brain capillary epithelial cells, thus allowing for enhanced drug absorption through the olfactory bulb and the blood-brain barrier.

In one embodiment, the biosurfactants of the present composition can suppress ROS to reduce damage caused by overproduction thereof.

In one embodiment, the biosurfactants of the present composition can inhibit P-glycoprotein, a cellular transporter that acts as a physiological barrier by extruding exogenous substances out of cells. This effect can help biosurfactants penetrate the blood-brain barrier, prevent P-glycoprotein-mediated drug efflux and assist any substrate molecules (e.g., therapeutic agents) in reaching and/or having a desired effect on the central nervous system.

In one embodiment, the biosurfactants of the present composition have significant antibacterial, antiviral and antifungal properties without being classified as antibiotics or antivirals.

The composition can further comprise one or more essential oils, botanicals, or other plant extracts comprising compounds with therapeutic antiviral, antibacterial, anti-biofilm, anti-inflammatory, and/or immunomodulatory properties, such as, for example, terpenes and/or phenols. These can include horseheal (*Inula helenium, L.* Asteraceae, elecampane), rose (*Rosa damascena L.*, Rosaceae), lavender (*Lavandula angustifolia L.*, Labiatae), chamomile (*Matricaria recutica L.*, Asteraceae), orange (*Rutaceae*), grapefruit (*Citrus paradisi*), eucalyptus (*Eucalyptus globulus L.* Myrtaceae), geranium (*Geranium robertianum L.*, Geraniaceae), juniper (*Juniperus communis L.*, Cupressaceae), citrus (*Citrus sinensis L.*, Rutaceae), tea tree (*Melaceuca alternifolia*), manuka bush (*Leptospermum scoparium*), neem tree (*Azadirachta indica, A. Juss*), tea plant (*Camellia sinensis*), rosemary (*Rosmarinus officinalis L.*, Lamiaceae), eucalyptus (e.g., *Eucalyptus globulus*), clove (*Syzygium aromaticum*), lemon, oregano, cinnamon, citronella, and thyme oils.

In a specific embodiment, the composition comprises about 0.1 to about 5 ml/L, about 0.2 to about 2 ml/L, or about 0.5 ml/L to about 1 ml/L each of *eucalyptus* oil, clove oil, and/or tea tree oil.

In some embodiments, the nasally-administered composition can further comprise one or more additional neuroprotective agents, such as antioxidants. Antioxidants include, for example, N-acetyl-L-cysteine, flavonoids, (e.g., anthocyanin, caffeic acid, catechin and quercetin), Vitamin E, tocotrienol, glucosinolates, isothiocyanates, and/or polyphenols. In certain embodiments, the composition comprises about 0.05 to about 1 gram/L, or about 0.1 to about 0.5 g/L of N-acetyl-L-cysteine.

The composition may have from 0.1% to about 99% (by weight or by volume) of one or more additional components including, for example, carriers, pH modifiers, buffers, chelators, local anesthetic agents, agents that promote wound healing, agents that help degrade biofilm, agents that stop bleeding and/or promote clot formation, carriers, and other therapeutic and non-therapeutic components, such as, for example, anti-viral agents, fungicidal agents, chemotherapeutic agents, topical antiseptics, anesthetic agents, oxygenated fluids and/or agents, diagnostic agents, homeopathic agents, and over-the-counter medications/agents.

In certain embodiments, the composition comprises a smoothing agent, such as glycerol or glycerin. In certain embodiments, the composition comprises an emulsifier, such as a salt selected from, for example, sodium chloride, sodium lactate, calcium lactate, sodium citrates, potassium citrates, calcium citrates, sodium phosphates, potassium phosphates, diphosphates, triphosphates, polyphosphates and tartrates.

In one embodiment, the components of the composition are formulated as a mixture, comprising optional additional ingredients, such as, for example, one or more carriers (e.g., pharmaceutically-acceptable carriers) and/or excipients.

The term "pharmaceutically acceptable" as used herein means compatible with the other ingredients of a pharmaceutical composition and not deleterious to the recipient thereof.

Carriers and/or excipients can be formulated into preparations in, for example, solid, semi-solid, liquid or gaseous forms, such as tablets, capsules, powders, granules, ointments, gels, lotions, solutions, suppositories, drops, patches, injections, inhalants and aerosols.

Carriers and/or excipients according the present invention can include any and all solvents, diluents, buffers (e.g., neutral buffered saline, phosphate buffered saline, or optionally Tris-HCl, acetate or phosphate buffers), oil-in-water or water-in-oil emulsions, aqueous compositions with or without inclusion of organic co-solvents suitable for, e.g., IV use, solubilisers (e.g., Tween 80, Polysorbate 80), colloids, dispersion media, vehicles, fillers, chelating agents (e.g., EDTA or glutathione), amino acids (e.g., glycine), proteins, disintegrants, binders, lubricants, wetting agents, emulsifiers, sweeteners, colorants, flavorings, aromatisers, thickeners, coatings, preservatives (e.g., Thimerosal, benzyl alcohol), antioxidants (e.g., ascorbic acid, sodium metabisulfite), tonicity controlling agents, absorption delaying agents, adjuvants, bulking agents (e.g., lactose, mannitol) and the like.

In some cases, the carriers can be, for example, sterile or non-sterile aqueous or non-aqueous solutions, suspensions, and emulsions. Examples of non-aqueous solvents include, without limitation, propylene glycol, polyethylene glycol, vegetable oils, and organic esters. Aqueous carriers include, without limitation, water, alcohol, saline, and buffered solutions. Acceptable carriers also can include physiologically acceptable aqueous vehicles (e.g., physiological saline) or other known carriers appropriate to specific routes of administration. The use of carriers and/or excipients in the field of drugs and supplements is well known. Except for any conventional media or agent that is incompatible with the supplement composition or with, its use in the present compositions may be contemplated.

Further components can be added to the compositions as are determined by the skilled artisan such as, for example, viscosity modifiers, preservatives, flavorings, dyes and other ingredients specific for an intended use. One skilled in this art will recognize that the above description is illustrative rather than exhaustive. Indeed, many additional formulations techniques and pharmaceutically-acceptable excipients and carrier solutions suitable for particular modes of administration are well-known to those skilled in the art.

In one embodiment, the pH of the formulations is between about 5.0 and 9.0, between about 5.5 and 8.5, between about 6.0 and 8.0, or between about 6.5 and 7.5.

In one embodiment, the subject invention provides a delivery system, wherein the BAM of the composition form a liposome or nanocapsule with the other components of the nasally-administered composition encapsulated therein. In one embodiment, additional biological polymers can be included to provide further structure for the nanocapsule.

This delivery system can enhance the bioavailability of therapeutic compounds by protecting the compounds from components in the blood, such as proteins and other molecules, that otherwise might bind to and/or degrade the compounds and prevent them from arriving at a target site, e.g., the brain. Additionally, the nanocapsule delivery system allows for time release of therapeutic compounds, thereby providing longer lasting therapeutic effects while reducing potential toxicity or potential negative side-effects of compounds in a subject.

In some embodiments, the composition further comprises a therapeutically-effective dose of an additional active ingredient, chemical and/or pharmaceutical compound.

In certain embodiments, pharmaceutical compounds can include those typically used for treating the symptoms and/or comorbidities of neurological conditions, for example, levodopa, tacrine, donepezil, rivastigmine, galanthamine, memantine, riluzole, edaravone, tetrabenazine, haloperidol, cimetidine, risperidone, quetiapine, amantadine, levetiracetam, clonazepam, beta interferons, ocrelizumab, glatiramer acetate, dimethyl fumarate, fingolimod, teriflunomide, natalizumab, alemtuzumab, and others such as dopamine agonists, MAO inhibitors, anticholinergic agents, cholinesterase inhibitors, antipsychotic drugs, steroids, corticosteroids, muscle relaxants, antidepressants, chemotherapeutic agents, SSRIs and anti-inflammatory compounds.

Naturally-derived substances that have been used for promoting cognitive health can also be included, such as, for example, resveratrol, ginger, curcumin, turmeric, licorice, ginseng, sage, rosemary, ginkgo, chamomile, willow bark, stinging nettle, maca, lemon, saffron and kava.

In one embodiment, the composition can be made into aerosol formulations so that, for example, it can be nebulized or sprayed. Suitable pharmaceutical formulations for administration in the form of aerosols or sprays are, for example, solutions, suspensions or emulsions. Formulations for nasal aerosol administration may also be formulated with illustrative carriers, including, for example, saline, polyethylene glycol or glycols, DPPC, methylcellulose, or in mixture with powdered dispersing agents or fluorocarbons. Aerosol formulations can be placed into pressurized propellants, asuch as dichlorodifluoromethane, propane, nitrogen, fluorocarbons, and/or other solubilizing or dispersing agents known in the art.

Methods

The present invention provides a method of preventing and/or treating a neurological condition, and/or its cause or symptoms wherein the method comprises administering a therapeutically-effective amount of a composition according to the present invention to a subject in need thereof.

As used herein, "administering" a composition or product refers to delivering it to a subject such that it contacts a target or site such that the composition or product can have an effect on that target or site. Administration can be acute or chronic (e.g., daily, weekly, monthly, etc.) or in combination with other agents. The present composition can be administered by any route of administration provided it is formulated for such a route. In this way, the therapeutic effects attainable by the methods and compositions of the invention can be, for example, systemic, local, tissue-specific, etc., depending of the specific needs of a given application of the invention.

In preferred embodiments, the compositions of the composition are delivered to the CNS via the upper portions of the nasal cavity, where the olfactory neurons are located. The olfactory bulb is closely connected to the cerebrospinal fluid (CSF), thus providing a route for nasally-administered therapeutic compounds to the brain and other parts of the CNS.

In preferred embodiments, the composition is formulated as a liquid or powder. The composition can be applied directly into the olfactory region, for example, using a syringe with an extended tube connected to the needle. In some embodiments, the composition is applied using a nebulizer, an atomizer, a particle metered dose inhaler (pMDI), or a dropper. In some embodiments, the composition is applied using an exhalation powered nasal device.

In preferred embodiments, one dose of the composition is administered through one of the subject's nostrils and/or both of the subject's nostrils, about 1 to 6 times per day, about 2 to 5 times per day, or about 4 to 5 times per day.

In certain embodiments, one dose will comprise about 0.01 ml to 5 ml, 0.05 ml to 2 ml, 0.07 ml to 1 ml, or about 0.1 ml to 0.5 ml of the composition.

In some embodiments, administration of the composition occurs daily for several days or longer. Factors to be considered when determining the number of doses to administer include the age of the individual receiving treatment and the severity of the subject's symptoms.

In certain embodiments, the composition is left at the site after administration thereto. In a further embodiment, the nasal cavity is rinsed with, for example, a sterile solution free of the active agent. Examples of solutions free of the active agent include, but are not limited to, plain water, saline, and isotonic solutions free of the active agent. The rinsing can be performed by administering the solution free of the active agent to the site and removing the resultant solution from the site or the tissue by, for example, suction or lavage. In certain embodiments, the rinsing is performed within about 1 minute to about 10 minutes, about 2 minutes to about 5 minutes, or about 3 minutes from the time of administering the composition to the site in the subject. In other embodiments, suction is performed, with or without rinsing.

In one embodiment, the method further comprises performing follow-up tests on the subject to determine whether, and/or to what extent, the condition/symptoms have been treated. The subject can be monitored throughout the course of treatment, for example, every day or every other day, in order to determine the treatment status and whether the composition is effective. This can include, for example, performing tests, such as those used for diagnosing the underlying neurological condition(s), as well as observing the subject for signs of improving health. If follow-up tests show that the rate of improved health is below that which is desired, the dosage of the composition can be adjusted as determined by the skilled practitioner.

Doses for use in the methods according to the subject invention may vary depending upon whether the treatment is therapeutic or prophylactic, the onset, progression, severity, frequency, duration, the type pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history).

Once improvement of the subject's condition has occurred, a maintenance dose can be administered if necessary. Subsequently, the dosage or the frequency of administration, or both, may be reduced to a level at which the improved condition is retained. When the symptoms have been alleviated to the desired level, treatment should cease. Subjects may, however, require intermittent treatment on a long-term basis upon any recurrence of symptoms.

In some embodiments, the method comprises diagnosing the subject with a neurological condition and/or a symptom thereof prior to treating the subject according to the present invention. Neurological conditions include, for example, infections affecting the brain and/or nervous system, neurodevelopmental diseases, and neurodegenerative diseases.

The term "symptom" as used herein means an abnormal occurrence in a subject that signals the presence of a disease or condition. Common symptoms of neurological conditions include but are not limited to brain inflammation; seizures and/or epilepsy; dementia; memory loss; language disorders; disorientation; mood swings; loss of motivation; anti-social behavior; behavioral issues; insomnia; loss in brain matter; loss in bodily function and/or control; and others.

In some embodiments, "symptom" includes the phrase "comorbidities," which are diseases or conditions present simultaneously with a neurological condition, such as anxiety; attention deficit disorder; clinical depression; Tourette syndrome; Fragile X syndrome; obsessive-compulsive disorder; bipolar disorder; learning disabilities; sensory disorders; developmental coordination disorder; disorders of the immune system and/or gastrointestinal system, including candidiasis; and/or addiction.

In some embodiments, the subject is diagnosed with neurological inflammation due to, for example, head trauma, nerve damage, cancer (e.g., a brain tumor), an allergic reaction, a food sensitivity, a neurodevelopmental disease, a neurodegenerative disease, and/or due to an infection of the nervous system or other part of the body. In some embodiments, the neuro-inflammation can be a cause and/or an effect of a neurological condition in the subject.

Advantageously, the materials and methods of the present invention can help improve the quality of life for individuals who are either suffering from a symptom of a neurological condition, or who are currently unaffected by a symptom but wish to prevent the occurrence and/or onset thereof.

Examples

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1

Nasally-Administered Composition for Treating Symptoms of Neurological Conditions A formulation of a nasal spray composition according one embodiment of the subject invention comprises the following components:

4 drops/L of *eucalyptus* oil
4 drops/L of clove essential oil
4 drops/L of tea tree oil
0.1 g/L of N-acetyl-L-cysteine
700 µg/ml of sophorolipid
20 ml/L of glycerol (for smoothing).
5 g/L of salt (for emulsification)

The composition is administered to the subject via the olfactory system, 4 to 5 times daily, until symptoms improve.

REFERENCES

Djupesland, P. G., et al. (2013). "Accessing the brain: the nose may know the way". J. Cereb. Blood Flow Metab. 33(5): 793-94.

Djupesland, P. G., et al. (2014). "The nasal approach to delivering treatment for brain diseases: an anatomic, physiologic, and delivery technology overview". Therapeutic Delivery. 5(6), 709-33.

We claim:

1. A method for treating neurological inflammation, the method comprising, administering, via the nasal cavity, a composition comprising a sophorolipid, a mannosylerythritol lipid, and an antioxidant, to a subject in need of such treatment, wherein the sophorolipid and the mannosylerythritol lipid are in the form of a liposome and the antioxidant is encased in the liposome, and wherein the neurological inflammation is caused by head trauma, a brain tumor, an allergic reaction, a neurodegenerative disease, or an infection.

2. The method of claim 1, wherein administration is carried out using a syringe, dropper, pump action nasal spray, nebulizer, atomizer, and/or an exhalation powered nasal device.

3. The method of claim 1, wherein the composition is administered to the subject 4 or 5 times daily.

4. The method of claim 1, wherein the composition further comprises glycerol and/or glycerin as a smoothing agent.

5. The method of claim 1, wherein the composition further comprises a salt as an emulsifier.

6. The method of claim 1, wherein the composition is formulated as a liquid or a powder.

7. The method of claim 1, wherein the composition is administered via the nasal cavity at a total volume of 0.01 ml to 5 ml per dose.

8. The method of claim 1, wherein the neurological inflammation is caused by a neurodegenerative disease.

9. The method of claim 1, wherein the antioxidant is N-acetyl-L-cysteine.

10. The method of claim 1, wherein the composition further comprises at least one plant extract or essential oil selected from the group consisting of *eucalyptus* oil, clove oil, and tea tree oil.

* * * * *